United States Patent [19]

Gates

[11] 4,213,342

[45] Jul. 22, 1980

[54] LIQUID SAMPLER DEVICE

[76] Inventor: Wendall C. Gates, Box 2216, Santa Cruz, Calif. 95063

[21] Appl. No.: 968,513

[22] Filed: Dec. 11, 1978

[51] Int. Cl.² ............................................. G01N 1/14
[52] U.S. Cl. ................................................. 73/421 B
[58] Field of Search ..................................... 73/421 B

[56] References Cited

U.S. PATENT DOCUMENTS

| 2,836,068 | 5/1958 | Clift | 73/421 B |
| 4,077,263 | 3/1978 | Brailsford | 73/421 B |

FOREIGN PATENT DOCUMENTS 597938  3/1978  U.S.S.R. ................................. 73/421 B

Primary Examiner—Gerald Goldberg
Assistant Examiner—Joseph W. Roskos
Attorney, Agent, or Firm—Owen, Wickersham & Erickson

[57] ABSTRACT

A device for taking a representative sample from a large volume of liquid in storage is disclosed. The device comprises a sealable sample container with fittings to facilitate attachment to the storage vessel to be sampled and a connected source of pressure controllable by valve means to cause movement of sampled liquid in and out of the sealed container. A filter unit connected to the sample container provides a trap for liquid or vapor that may be purged from the sample container as the sample is taken. The sample container has a control for providing automatic shutoff of sample flow when the sample container is filled. In one embodiment of the invention, source-pressure is utilized to create a suction for drawing liquid to be sampled into the sample container, and in a second embodiment, the source-pressure is used to purge the sample liner and its fittings prior to allowing the storage vessel pressure to force liquid into the sample container. The invention makes possible the taking of large-volume liquid samples without an explosion hazard and without exposing the operator to the liquid directly or otherwise releasing the chemical to the atmosphere.

18 Claims, 8 Drawing Figures

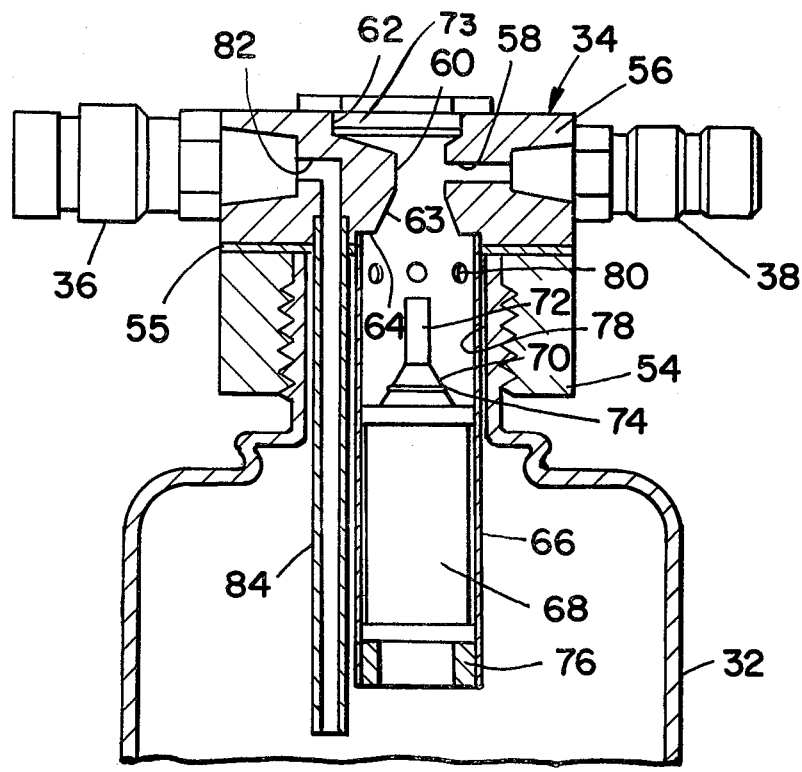
FIG_2
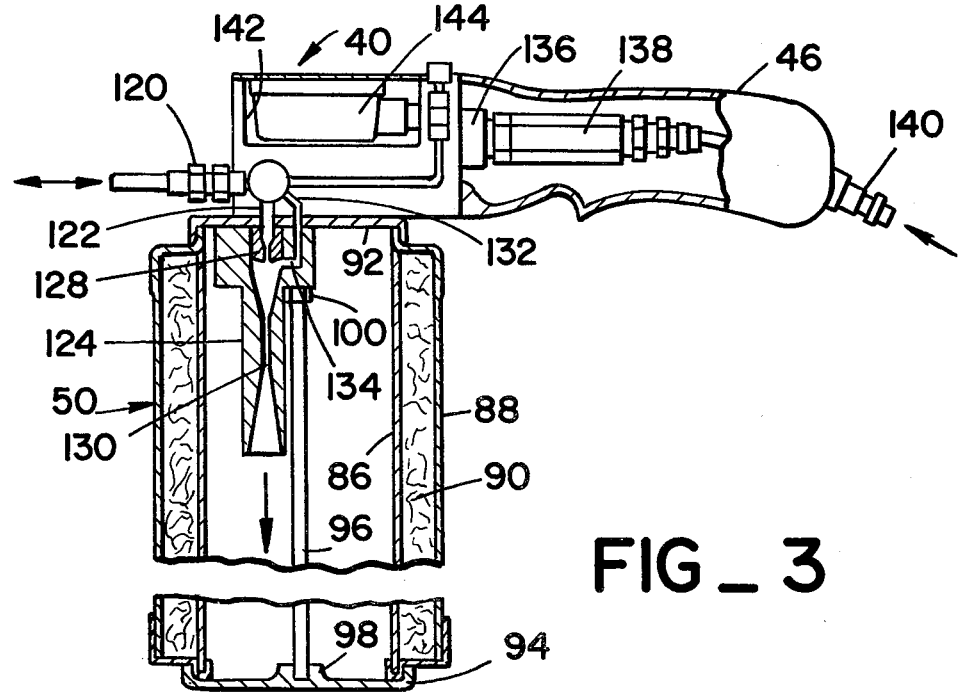
FIG_3

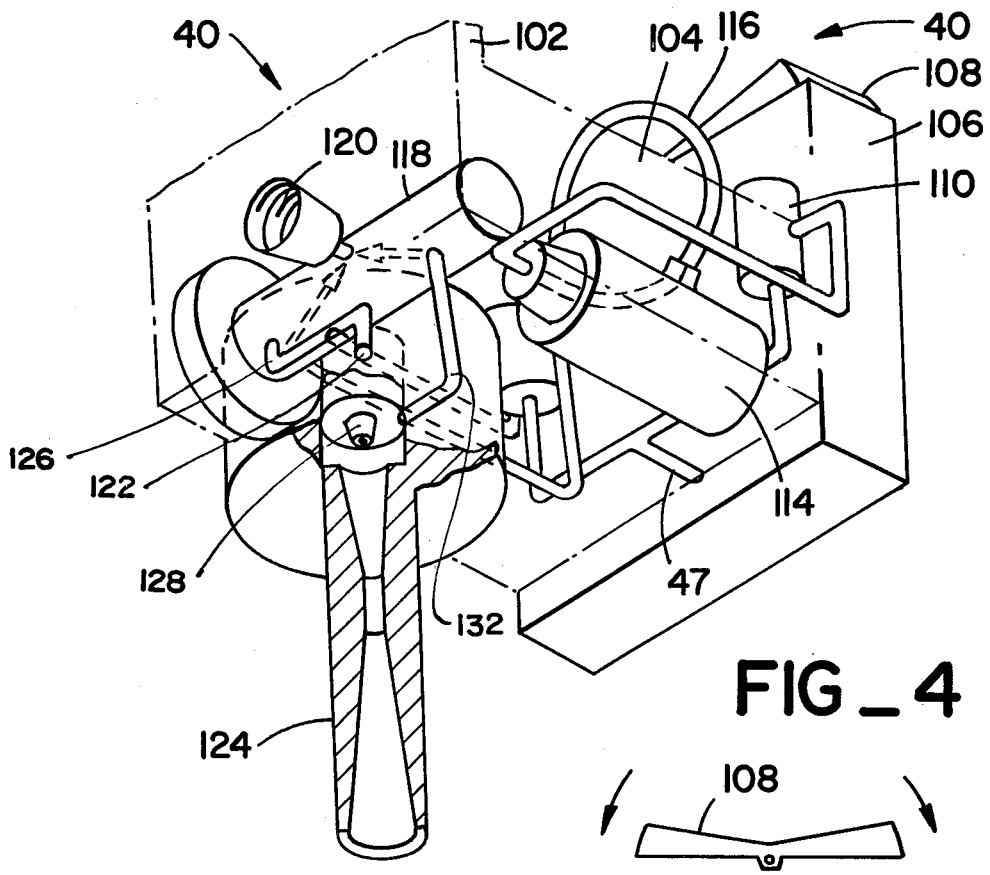
FIG_4
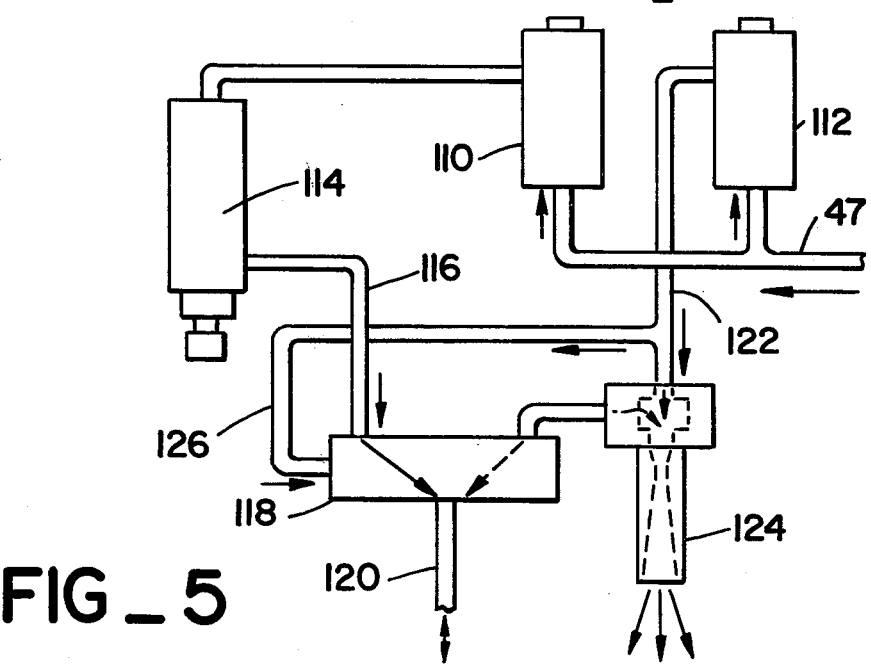
FIG_5

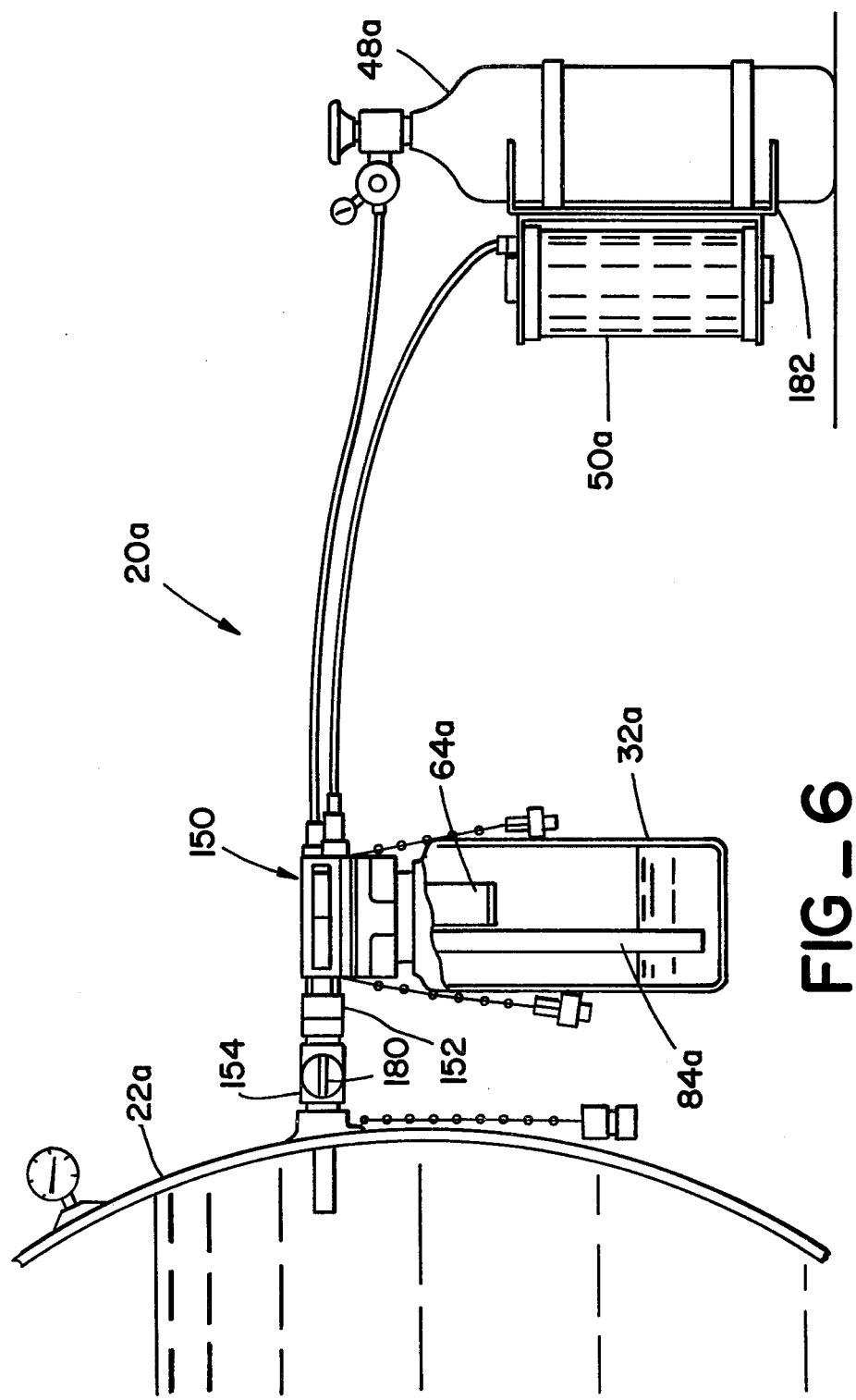
FIG_6

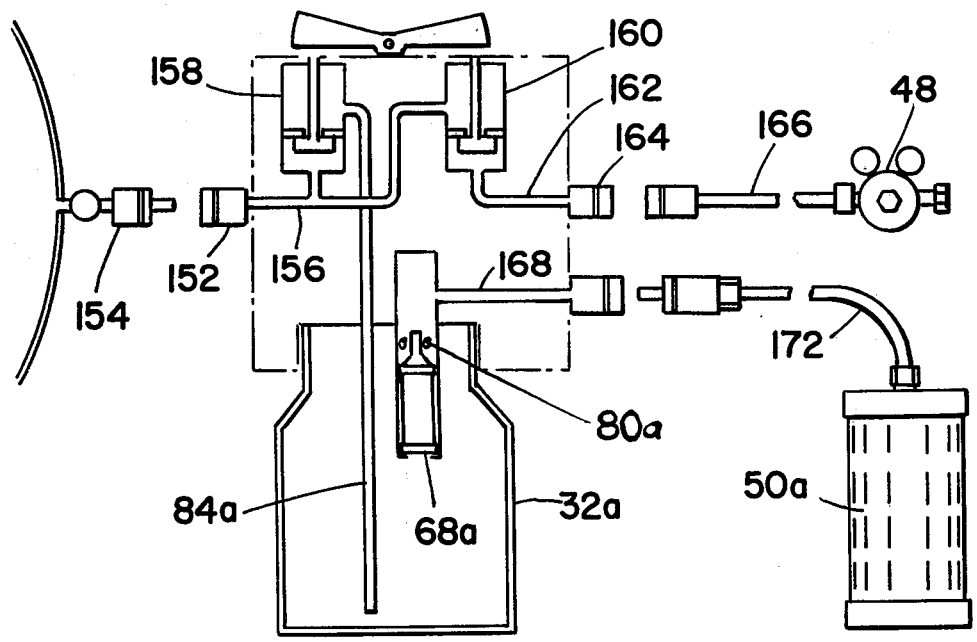
FIG_7
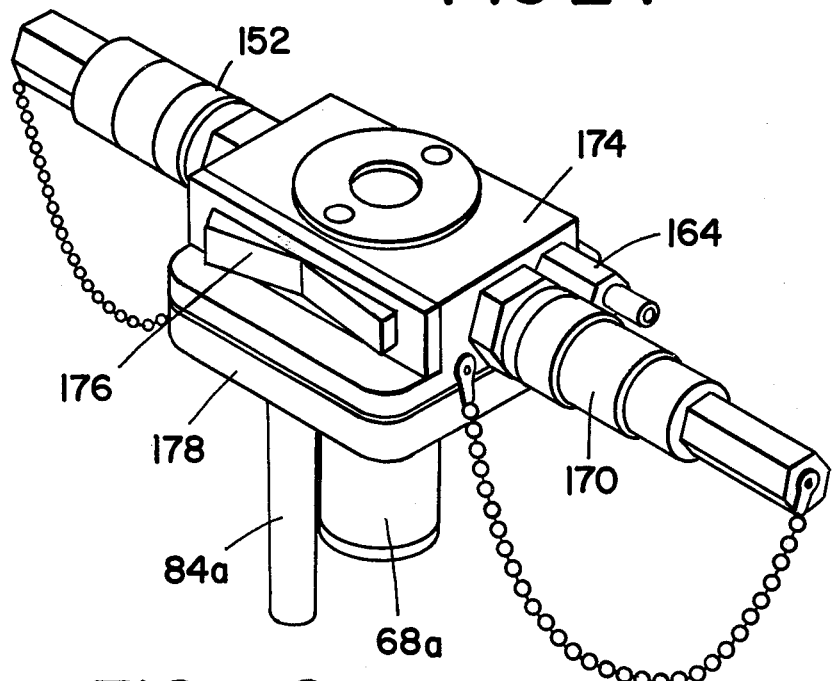
FIG_8

LIQUID SAMPLER DEVICE

BACKGROUND OF THE INVENTION

This invention relates to sampling devices and apparatus and more particularly to a device for enabling an operator to take a liquid sample for subsequent analyses without contacting the liquid or releasing it to the surrounding atmosphere.

Many liquids such as petroleum products and petrochemicals which are stored and transported in various tanks or containers in commerce must be sampled upon various occasions as when being sold. Existing legal and contractual requirements necessitate sampling according to procedures specified in the American Society for Testing and Materials (ASTM) D270-65. A typical procedure according to these standards is the so-called running method wherein an unstopped beaker or bottle is lowered from above the top level of the liquid (in a tank car, for example) to the level of the bottom of the outlet connection or swing line, and returning it to the top of the liquid at a uniform rate of speed such that the beaker or bottle is about three-fourths full when withdrawn from the oil.

With the discovery of carcinogenic effects of many industrial feedstocks, as well as the increasing use of more obviously toxic or flammable chemicals, it became essential to reduce or prevent entirely any worker exposure to such liquids during a sampling procedure. Yet, the volume of such liquids being transported in commerce steadily increased.

A similar problem of operator exposure was encountered in the taking of liquid samples from pipelines or other conduits. Consequently, an urgent need arose to provide an adequate apparatus that would enable a relatively unskilled worker to accomplish accurate sampling of a body of liquid in a tank, vessel, pipeline, or other containment while minimizing operator exposure to the liquid. The present invention solves this problem.

BRIEF SUMMARY OF THE INVENTION

In accordance with the principles of the present invention a sampling device is provided which is portable and can be readily operated by a single workman at the liquid tank being sampled. In broad terms, the device comprises a sealable sample container with a head unit having inlet and outlet fittings, the former facilitating its easy attachment to the liquid storage vessel. The head unit also includes an automatic shutoff valve that closes and provides a visual indication when the sample container is filled. Connected to the outlet fitting on the head unit for the sample container is a pressure source, preferably in the form of an inert compressed gas or air. The compressed gas is furnished through a controllable valve unit attached to a vapor trapping filter. The valve can be operated initially to purge the sample line and its fitting in a preliminary operating mode, causing the purged vapor or liquid to move into the storage vessel. Thereafter, the valve is manipulated to a second mode to create a suction or pressure force that moves liquid from the storage tank into the sample container. A final purge of compressed gas is used to again clean out the storage line and fittings of the device, permitting uncoupling of the fittings without spillage.

In summary, one object of the present invention is to provide a device for taking liquid samples from a storage vessel without exposing the operator of the device to the liquid being sampled or otherwise releasing the liquid or vapor into the surrounding atmosphere.

Another object of the invention is to provide a sampling device as described that includes a sample container having an automatic shutoff with means for sealing it to prevent any escape of the sample liquid during its transportation to a laboratory prior to its analysis.

Another object of the invention is to provide a liquid sampling device that can purge the sample line and fittings prior to disconnecting the sample container from the storage container so as to prevent any purged liquid or vapor from escaping to the atmosphere.

Still another object of my invention is to provide a liquid sampling device that can utilize a pressurized gas to create a suction for extracting a liquid sample from various types of tanks or source vessels from which it is necessary to lift the liquid to obtain a sample.

Other objects, advantages and features of the invention will become apparent from the following detailed description presented in conjunction with the accompanying drawing.

BRIEF DESCRIPTION OF THE DRAWINGS

FIG. 2 is an enlarged fragmentary view in elevation and partially in section showing the sample container and its head unit for the device of FIG. 1;

FIG. 3 is an enlarged fragmentary view in elevation and partially in section showing the vapor trapping filter and the attached control unit for the device of FIG. 1;

FIG. 4 is a somewhat schematic view in perspective showing the control unit with its attached ejector nozzle for the device of FIG. 1;

FIG. 5 is a diagrammatic view showing the flow path through the control unit of FIG. 4;

FIG. 6 is a view in elevation showing a modified form of sampler device according to the present invention;

FIG. 7 is a diagrammatic view of the sampler device of FIG. 6; and

FIG. 8 is a view in perspective of the control unit for the device of FIG. 6.

DETAILED DESCRIPTION OF EMBODIMENTS

Figure 1:
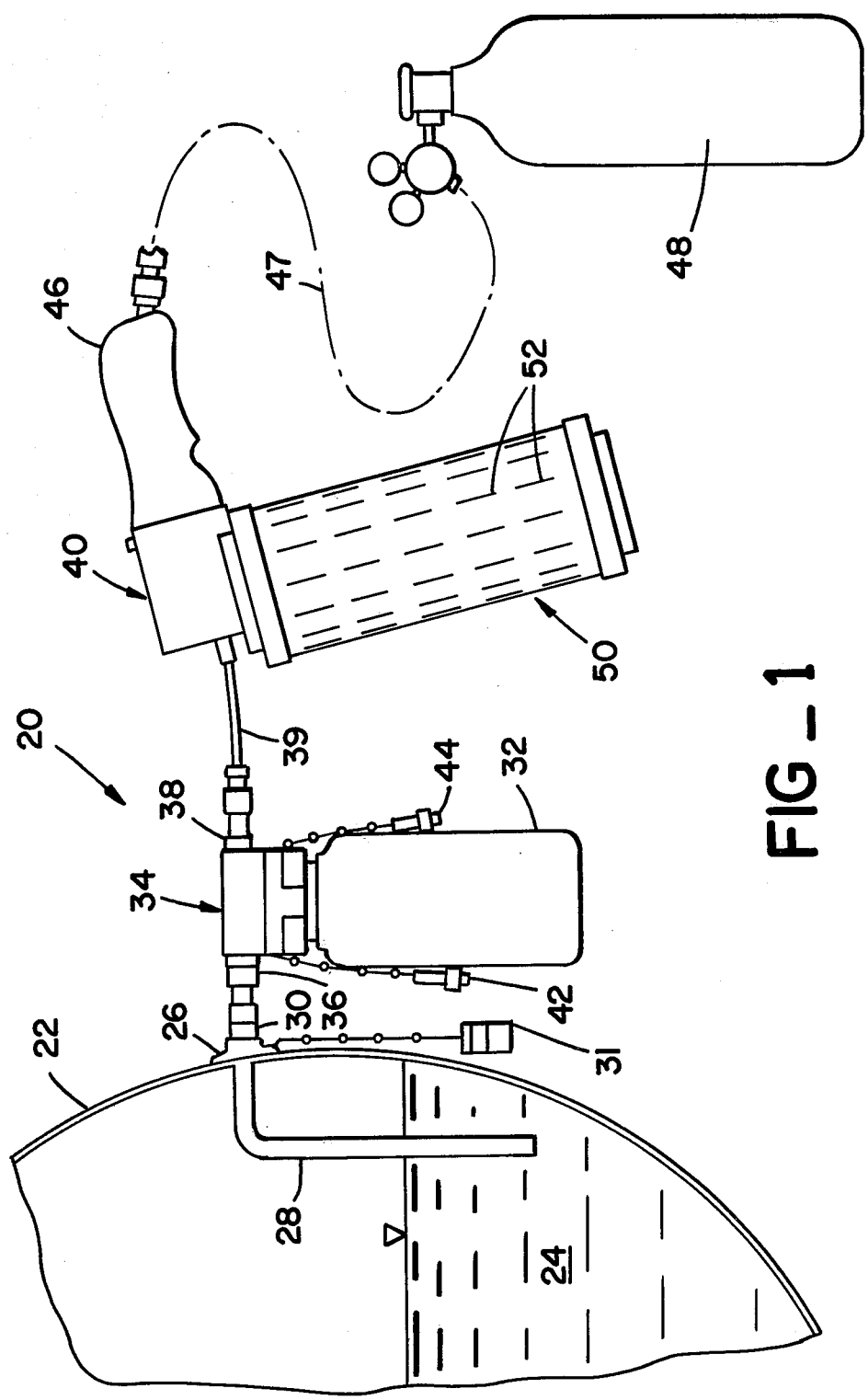
FIG. 1 is a view in elevation showing a sampler device according to the invention as it appears in operation and connected to a liquid storage tank.

With reference to the drawing, FIG. 1 shows a liquid sampling device 20 embodying principles of the present invention as it appears when connected to a typical storage vessel 22 such as a railroad tank car for taking a sample therefrom. In this embodiment, the liquid 24 to be sampled is at a level that is below a vessel outlet opening 26 to which is connected a downwardly extending standpipe 28, in the conventional manner. On the outside of the storage vessel, the outlet opening is provided with a suitable fitting 30 for a removable plug 31 to which the sampling device 20 can be quickly and easily connected when the plug is removed.

In general, the sampling device comprises a sample container 32 for retaining the liquid sample to which is attached a sampling head 34. The sampling head has an inlet fitting 36 adapted to connect with the fitting 30 on the storage container and an outlet fitting 38 connected by a flexible conduit 39 to a control unit 40. A pair of protector plugs 42 and 44, each preferably retained by a chain anchored to the sampling head, are provided for closing the inlet and outlet fittings 36 and 38 after the sample container has been filled and its contents ready for analysis. The control unit 40 is connected through a handle portion 46 attached by a conduit 47 to a source of compressed gas (e.g. instrument air, $CO_2$, blanket gas) represented by the conventional storage cylinder 48. Also attached to the control unit 40 is a canister 50 for a vapor-trapping filter having a series of vent openings 52 through which purged and filtered air can pass.

The sample container 32 and its sampling head 34 are shown in greater detail in the cross-sectional view of FIG. 2. The container may be made of any suitable material such as plastic, metal or glass, and it preferably is formed with an open top adapted to receive and retain the sampling head. The head itself, which may be formed from metal, molded plastic, or some other suitable material, comprises a lower collar portion 54, a gasket 55, and an upper manifold assembly 56 held to the collar portion by suitable screws (not shown). The inlet and outlet fittings 36 and 38 are fixed to the manifold assembly. The outlet fitting 36 is aligned with a horizontal passage 58 in the manifold which intersects a larger, centrally located vertical passage 60 that forms an opening 62 on the upper surface of the sampling head. Below the horizontal passage, the vertical passage has a conical surface 63 and then terminates as a larger cylindrical surface that forms a seat 64 for a tubular sleeve member 66 that extends downwardly into the sample container. This sleeve member serves as a housing and guide for a shutoff float 68 which has a generally cylindrical shape and fits slidably within the sleeve member. On the upper end of the float is a frusto-conical portion 70 that tapers down to a smaller upper cylindrical stem portion 72, preferably having a distinctive color such as red, that is easily noticeable. A window 73 in the opening 62 is provided in the top surface of the manifold for observing this stem. An annular O-ring 74 is seated within the outer surface of the conical-shaped portion 72 and forms a fluid seal with the conical-shaped surface 63 of the vertical passage when the float is forced upwardly into it. Fixed to the inside lower end of the tubular member is an annular seat 76 that retains the float when the sample container is empty. This annular seat may also contain a coiled spring (not shown) as a counterbalance to improve the sensitivity of the float.

Near its upper end, the tubular sleeve member is spaced inwardly from the inner wall surface 78 of the upper throat portion 54 of the sample container, and at this location the sleeve member 66 has a series of holes 80 that allow vapor to escape through the inlet fitting as the sample container is filling up.

The inlet fitting 38 is aligned with a passage 82 in the manifold that extends downwardly and forms a seat for a liquid inlet tube 84 that extends below the guide sleeve member 66 for the float.

Turning now to FIG. 3, the combined control and vapor trapping unit 40, as shown, comprises a series of connected blocks forming fluid passages attached to the cylindrical adsorber canister 50. This canister has a thin inner perforated wall 86 spaced inwardly from an outer wall 88 having the vents 52. These walls form an annular container that is packed with a filter material 90 such as activated carbon. A pair of upper and lower circular disks 92 and 94 forming opposite end walls of the canister are held together by a centrally located rod 96. The rod is threaded to an internal boss portion 98 of the lower disk and is secured to the upper disk by a pair of hexnuts 100.

As shown schematically in FIG. 4, the control unit 40 attached to the vapor trapping canister 50 is comprised of a front block 102, a center block 104, and a back block 106 which are held together by suitable screws (not shown). The back block forms a seat for a rocker switch 108 mounted at a central pivot point in the conventional manner so that it can be pushed in one direction to operate a first valve 110 and in the opposite direction to operate a second valve 112. These valves are conventional spring loaded poppet-type valves that fit within suitable cavities within the back block and are connected within appropriate inlet passages to receive compressed gas from the supply source 48 when actuated. As shown diagrammatically in FIG. 5, the first valve 110, for use in the purge mode, is connected by an outlet passage through the center block to a pressure regulator 114. The outlet from the pressure regulator passes through a short piece of tubing 116 and provides gas at a reduced pressure through the front block through a three-way valve 118 and out through an orifice and fitting 120 to purge any vapor trapped in the sampling head 34 and the sample line to the storage vessel.

The second valve 112 in the back block 106 of the control unit 40 has an outlet passage aligned with a passage in the center block and with another passage in the front block. This passage provides an inlet to a pressure port 122 of an injector-type vacuum pump 124, and a branching passage 126 provides a pilot input to control the three-way valve 118. The vacuum pump comprises first and second convergent-divergent nozzles 128 and 130 in tandem and is fixed to the underside of the upper disk 92 so that the outlet from the second nozzle is open within the adsorber canister 50. The three-way valve is also connected by a passage 132 to a suction port 134 of the vacuum pump located between the two nozzles. Pressurized gas forced through the first nozzle 128 causes sonic flow in the conventional manner and creates a suction at the port 134 which is transmitted back to the sample container.

The back block has an inlet fitting 136 connected to a conventional dirt filter 138 that is housed within the handle 46 as shown in FIG. 3. A quick disconnect fitting 140 is fixed to the dirt filter for the conduit 47 that extends from the rear end of the handle to connect with the source of pressurized gas.

The center block of the control unit is lower than the front and back blocks, thereby forming a recess 142 for retaining pressure indicator gauge 144 connected to the pressure input port.

In operation, the device 20 is first connected to the storage tank to be sampled by connecting the inlet fitting of the sampling head to the supply tank's exterior fitting. Next, the filter and the control unit (connected to the pressurized gas bottle) is coupled to the outlet fitting of the sampling head. At this point, it may be assumed that gas from the pressure source is being supplied through the dirt filter 138 in the handle 46 to the rocker switch valves 110 and 112 of the control unit 40. Now, the rocker 108 is first depressed to operate the first or purge valve 110. This causes the relatively high pressure supply gas to flow through the pressure regulator 114 so that relatively low pressure gas (6 psig) will flow through the three-way valve 118 and out the tube 39 to the sampling head 34. The three-way valve prevents any venting of purged pressure through the vacuum generator and the low pressure purging gas clears out stale liquid from the sample line. This purging may be accomplished in a matter of seconds and when completed the rocker is moved in the opposite direction, thereby closing the first valve 110 by virtue of its spring return action and opening the second valve 112. This supplies the pressurized supply gas to the injector-type vacuum pump 124 and also via the pilot passage 126 to the three-way valve 118. The pilot pressure opens the three-way valve to the conduit from the sampling head and the injector pump thereby creates a suction in the sample container. As a result, the liquid from the supply tank is drawn through the inlet fitting into the supply container. As the liquid level rises in the sample container the float 68 is pushed upwardly. Any vapor or air in the sample container escapes first through the openings 80 at the upper end of the tube. The float continues upwardly until the sample container is filled and the float seats and seals within the conical surface 63 of the vertical passage in the sampling head.

As the upper edge of the cylindrical portion of the float passes the small holes 80 in the upper end of the guide tube the passage of vapor is greatly reduced creating a lower pressure in the space above the float. The combination of reduced pressure above and buoyant force below causes the float to jump suddenly upwardly into its seat. This sudden jump improves the sealing action and gives a distinct, sharp indication of filling. With the float thus seated, the upper stem 72 is visible through the opening of the sampling head and provides an indication that the sample container is filled.

The vapor drawn from the sample container as it is filled flows through the connecting tube 39 and through the 3-way valve 118 in the control unit 40 and into the vapor trapping canister 50. Here it is neutralized and/or filtered before the trapped air is expelled through the vents 52 in the outer wall of the canister.

While the device 20 as just described is most useful where the level of the liquid in a storage vessel is below its outlet and the vessel is not pressurized, the present invention embodied in a somewhat modified device 20a may also be used where the liquid level in a storage vessel 22a is above its outlet. As shown in FIG. 6, this modified device comprises a container 32a having an inlet tube 84a that extends to near the bottom of the container and a float member 68a that rises during and indicates when the sample container is filled. Fixed to the top of the container is a head member 150 having an inlet fitting 152 which is adapted to connect with a mating fitting 154 on the outlet from the storage vessel 22a. This inlet fitting is connected to a passage 156 in the head member which communicates with the inlet tube 84a of the sample container through a flow valve 158, as shown schematically in FIG. 7. The inlet passage is also connected to the output side of another flow valve 160 whose input side is connected through a passage 162 to a fitting 164 on the head member. This latter fitting is connected via a conduit 166 to a source 48 of compressed gas, as in a conventional gas cylinder.

As with the suction-type sampling device 20, the float member 68a is supported within a tubular guide 78a. Near its upper end, the guide also has a series of holes 80a to allow vapor to escape through a passage 168 in the head member to an outlet fitting 170. This latter fitting is connected by a conduit 172 to a canister 50a which is similar to the canister 50 of the device 20, i.e., having previous inner and outer walls supporting a thickness of filtering and chemical neutralizing material 90.

In FIG. 8, a perspective view of the head member 50 in a preferred form is shown wherein the valves 158 and 160 are enclosed within a compact housing 174 and are actuated by an external rocker switch 176. The housing is fixed to an adapted collar 178 that functions to attach the head member to the container 32a. The inlet tube 84a and the float member 68a extend through and downwardly from the adapted collar 178.

In operation when a sample is to be taken from a storage tank 22a whose liquid level is above its outlet, as shown in FIG. 6, the outlet fitting 154 is first connected to the mating outlet fitting 152 on the tank. The tank fitting is provided with a shutoff valve 180 that is closed during this connection. Now, the rocker switch 176 on the sample head 150 is moved to the purge position so that compressed gas flows from the pressure source, through the sample head and through its inlet fitting. When the shutoff valve 180 is opened, the compressed gas flows to purge the sample head and the inlet conduit of all unwanted liquid or vapor. The purge cycle may last for several seconds and when completed, the rocker switch is moved to the sample taking mode. Thus, the purge valve 160 is closed by its spring action and the sample taking valve 158 is opened, thereby causing liquid to flow from the storage tank through the inlet fitting 152, the valve 158 and into the inlet tube 84a within the sample container 32a. As this container fills up, the float 68a rises within its guide sleeve, forcing out the air and vapor and eventually seating at the stop in the same manner as shown in FIG. 2. When the float has reached its upper limit, its upper stem position 72 is visible to indicate a full sample container, as previously described. At this point, the rocker switch is turned back to the purge position to clear the sample container inlet fittings, and as this is done, the shutoff valve 180 on the supply tank should be closed. The air and vapor forced from the sample container as it is filled with liquid is trapped within the canister 50a which may be conveniently attached to the compressed gas cylinder 48a by a suitable bracket 182 within the canister. The possibly harmful vapor is neutralized before passing through a wall of activated chemically filtering material in the same manner as with canister of the device 20. With the shutoff valve 180 on the supply tank closed, the sampled container can be uncoupled from it and from the canister and compressed gas cylinder. The plugs for the inlet and outlet fittings on the sample container head are now connected in place to assure no spillage, and the sample container can be transported to a suitable facility for testing.

From the foregoing, it is apparent that the present invention provides a device for sampling liquids that may be toxic or harmful from supply vessels wherein the liquid level is below or above the vessel outlet. Moreover, the liquid sample can be captured without releasing harmful vapor or without requiring the sample taker to contact the liquid in any way.

To those skilled in the art to which this invention relates, many changes in construction and widely differing embodiments and applications of the invention will suggest themselves without departing from the spirit and scope of the invention. The disclosures and the description herein are purely illustrative and are not intended to be in any sense limiting.

I claim:

1. A device for taking liquid samples from a storage tank or other liquid containment while minimizing the exposure of the sample taker to the liquid or vapor therefrom, said device comprising:

A. a sample container with an opening at one end;
B. head means on said container covering said opening and having inlet means and outlet means for said container, said inlet means being adapted to be connected to an outlet from a vessel or conduit from which a sample is to be taken;
C. movable float means within said container and operative in response to the filling of said container for forcing out vapor through said outlet means and closing said outlet means when said container is substantially full of liquid;
D. filter means connected to said container outlet for trapping the vapor forced from said container as it is filled with liquid;
E. and control means adapted for connection to a source of gas under pressure and including a first valve means operable for forcing a purging stream of compressed gas from said source through said container head means and its inlet means, and a second valve means operable after closure of said first valve means for admitting liquid from the vessel or conduit through said inlet means into said sample container.

2. The device as described in claim 1 wherein said control means further includes a nozzle means through which pressurized gas is directed by said second valve means, and means interconnecting said nozzle means with said sample container so that a suction force is created to draw liquid from the storage tank into said sample container.

3. The device as described in claim 1 wherein said filter means comprises inner and outer pervious and spaced apart wall members for retaining an annular body of filtering material.

4. The device as described in claim 2 wherein said nozzle means is located within said filter means.

5. The device as described in claim 2 wherein said nozzle means comprises a first convergent-divergent nozzle in tandem with a second and larger convergent-divergent nozzle; said interconnecting means from said sample container having an outlet opening between said nozzles.

6. The device as described in claim 2 wherein said control means is fixed to the top of and extends downwardly therefrom into said filter means.

7. The device as described in claim 2 wherein said control means is fixed to said filter means and includes a pressure regulator means connected by a passage to said first valve and to a three-way valve whose outlet is connected to said sample container; and passage means connecting said second valve means to said three-way valve; and to said nozzle means, whereby actuation of said first valve means provides relatively low pressure purge air through said three-way valve and actuation of said second valve means provides relatively high pressure air to said nozzle means.

8. The device as described in claim 1 wherein said sample container has an inlet tube connected to said inlet means of said head means and extending to near the bottom of said sample container, and guide means for said movable float means adjacent said inlet tube.

9. The device as described in claim 1 wherein said float means has a generally cylindrical shape with a frusto-conical upper portion with an upwardly extending stem fixed thereto, said stem being visible above said head means to provide an indicator when the sample container is substantially full.

10. The device as described in claim 1 wherein said float means is generally cylindrical and is slidable with a tubular sleeve within said sample container, said tube having a series of holes hear its upper end and aligned with a vertical opening in said head means that communicates with said outlet means connected to said filter means.

11. The device as described in claim 10 wherein said holes in said sleeve are located so that they are closed by said cylindrical float means as it rises, thereafter causing a reduced pressure above said float means that causes it to jump suddenly upwardly into its seat to form a fluid tight seal.

12. A device for taking liquid samples from a storage tank or other liquid containment while minimizing the exposure of the sample taker to the liquid or vapor therefrom, said device comprising:

A. a sample container with an opening at one end;
B. head means on said container covering said opening and having inlet means to said container and outlet means, said inlet means adapted to be connected to the outlet of a vessel or conduit from which a sample is to be taken;
C. movable float means within said container and operative in response to the filling of said container for forcing out vapor through said outlet means and closing said outlet means when said container is full of liquid;
D. filter means connected to said container outlet for trapping the vapor forced from said container as it is filled with liquid;
E. and control means connected to said filter means and adapted for connecting to a source of gas under pressure, said control means including a first valve means operable for forcing a purging stream of compressed gas from said pressure source through said container head means and its inlet means to said storage tank, a second valve means operable after closure of said first valve means and connected to a nozzle means extending into said filter means for sucking vapor from said sample container and passing it into said filter and simultaneously drawing liquid from the vessel or conduit through said inlet means into said sample container.

13. A device as described in claim 12 wherein said control means and said connected filter means are connected by a flexible conduit to said head means on said sample container.

14. A device as described in claim 12 wherein said first and second valve means are operated by a rocker switch on said control means.

15. A device as described in claim 12 wherein said float means has a generally cylindrical shape with an upper frusto-conical portion attached to an indicator means at its end, said frusto-conical portion being adapted to fit within and form a fluid tight seal with a conical surface in said outlet means of said head means.

16. A device as described in claim 12 wherein said nozzle means comprises first and second convergent-divergent nozzles in tandem, and passage means from said sample container having an opening between said nozzles.

17. A device for taking liquid samples from a storage tank or other liquid containment while minimizing the exposure of the sample taker to the liquid or vapor therefrom, said device comprising:

A. a sample container with an opening at one end;
B. head means on said container covering said opening and having inlet means to said container and outlet means, said inlet means being adapted to be connected to the outlet of a vessel or conduit containing liquid under pressure from which a sample is to be taken;
C. movable float means within said container and operative in response to the filling of said container for forcing out vapor through said outlet means when said container is full of liquid;
D. filter means connected to said container outlet for trapping the vapor forced from said container as it is filled with liquid;
E. and control means adapted for connection to a source of gas under pressure and including a first valve means operable for forcing a purging stream of compressed gas from said source through said container head means and its inlet means, and a second valve means operable after closure of said first valve means for admitting liquid from the vessel or conduit through said inlet means into said sample container until said float means has been raised to its closing position.

18. A device as described in claim 15 wherein said control means is attached to said head means on said sample container.

* * * * *